United States Patent [19]

Abrams

[11] Patent Number: 5,068,951

[45] Date of Patent: Dec. 3, 1991

[54] DEVICE FOR APPLYING CONSTANT PRESSURE TO A SURFACE

[75] Inventor: Eve M. Abrams, Rockville, Md.

[73] Assignee: The United State of America as represented by the Administrator, National & Space Administration, Washington, D.C.

[21] Appl. No.: 531,374

[22] Filed: May 31, 1990

[51] Int. Cl.[5] .............................................. B05C 17/02
[52] U.S. Cl. ................................... 29/110.5; 29/123; 29/132; 15/230.11
[58] Field of Search ....................... 29/110.5, 132, 133; 15/230.11; 118/DIG. 15, 201, 258, 264; 401/5, 197, 208

[56] References Cited

U.S. PATENT DOCUMENTS

| | | | |
|---|---|---|---|
| 580,982 | 4/1897 | Marster | 29/110.5 |
| 782,840 | 2/1905 | Fortier | 29/110.5 |
| 3,474,482 | 10/1969 | Burns et al. | 15/230.11 |
| 3,857,015 | 12/1974 | Clark et al. | 29/110.5 |
| 3,986,226 | 10/1976 | Roe et al. | 29/110.5 |
| 4,316,301 | 2/1982 | Smith et al. | 29/110.5 |
| 4,570,280 | 2/1986 | Roth | 29/110.5 |
| 4,742,597 | 5/1988 | LaFlamme | 29/110.5 |

Primary Examiner—Irene Cuda
Attorney, Agent, or Firm—R. Dennis Marchant; Harold W. Adams

[57] ABSTRACT

A device 10 for applying constant pressure to a surface includes a cylinder 12 having a longitudinal axis greater than the diameter of cylinder 12. A first wheel 14 and a second wheel 16 are coupled to each end 18 and 20, respectively, of cylinder 12. Wheels 14 and 16 have a diameter substantially greater than the diameter of cylinder 12. An elastomeric covering 22 surrounds cylinder 12. Elastomeric covering 22 has an outer diameter substantially greater than the diameter of wheels 14 and 16. A handle 24 is coupled to wheels 14 and 16 for rolling and applying pressure to elastomeric covering 22.

10 Claims, 2 Drawing Sheets

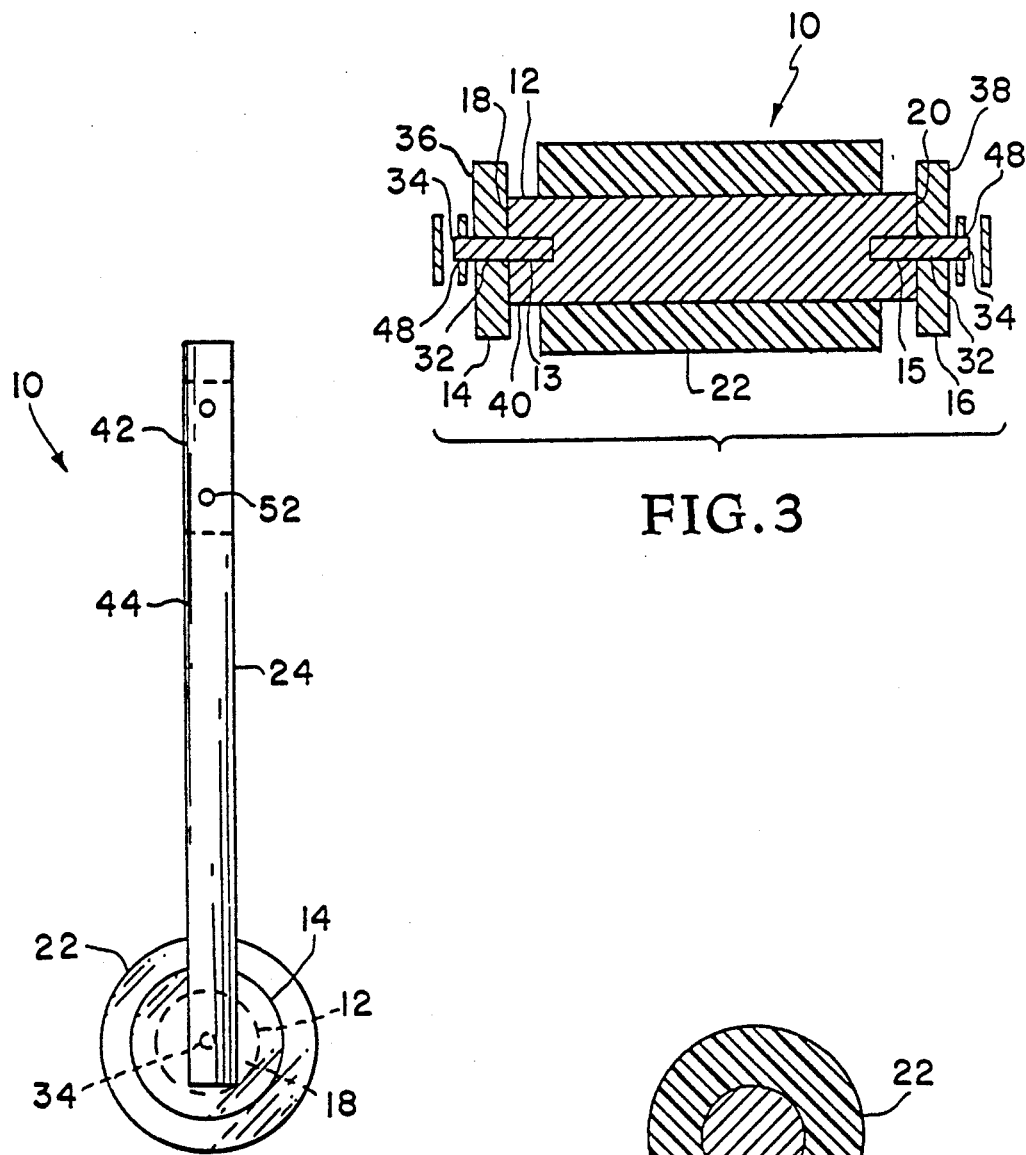

DEVICE FOR APPLYING CONSTANT PRESSURE TO A SURFACE

ORIGIN OF THE INVENTION

The invention described herein was made by an employee of the United States Government and may be manufactured and used by or for the Government for governmental purposes without the payment of any royalties thereon or therefore.

TECHNICAL FIELD

This invention relates generally to pressure rollers and more particularly to rollers for applying constant pressure to a surface.

In many industrial areas and space applications it is necessary to accurately analyze contamination particles that can accumulate on a surface. This is necessary to learn the type and amount of particulate contamination that a particular surface is subject to. Accordingly, a device is desired that will ensure that an accurate analysis of particulate contamination samples can be obtained. The prior art devices are unable to provide these requirements.

BACKGROUND ART

The customary manner of obtaining particulate contamination samples is to lay the sticky side of a tape to the surface that has particulate contamination on it and rub one's finger across the tape so that the particles stick to the tape. It is essential that the finger pressure be as constant as possible so that the same amount of particles will adhere to the length of tape. This of course is almost impossible to perform without varying the finger pressure. The tape is then removed and placed under a microscope where the number and size of the particles can be determined. This is not an optimum method because as the finger is moved across the tape, the amount of pressure will vary, which may cause an inaccurate analysis.

Another device used with the tape lift method for obtaining constant pressure is to roll a solid heavy roller over the tape. The disadvantage of this approach for use in tape lift sampling is that the roller does not conform to the surface imperfections which can cause portions of the particulate contamination samples not to be picked up. In addition, the pressure cannot be varied which may cause an inaccurate sample analysis and may crush the particulate contamination samples.

Accordingly, one object of the invention is to provide a device which will apply constant, predetermined pressure to a surface.

Another object of the invention is to provide a device which will conform to the imperfections of a surface.

A further object of the invention is to provide a device that will insure an accurate sample count using the tape lift method.

Still another object of the invention is to provide a simple device for applying constant pressure to a surface.

A still further object of the invention is to provide a simple device for accurately making a size and count determination of particulate contamination samples using the tape lift method.

Another object of the invention is to provide a constant pressure roller for applying constant pressure to the surface of an adhesive tape that will conform to the imperfections of the surface.

STATEMENT OF THE INVENTION

Briefly, these and other objects are obtained with a device for applying constant pressure to a surface. The device includes a cylinder having a longitudinal axis substantially greater than the diameter of the cylinder. First and second wheels are coupled to each end of the cylinder. The first and second wheels have a diameter substantially greater than the diameter of the cylinder. An elastomeric covering covers the cylinder and has an outer diameter substantially greater than the diameter of the first and second wheels. A handle is rotatably coupled to the first and second wheels to apply pressure to the elastomeric covering.

BRIEF DESCRIPTION OF DRAWINGS

In the drawings like parts are designated by the same references in the figures, wherein:

FIG. 2 is a side view of the preferred embodiment of the invention of FIG. 1.

FIG. 3 is a side view in cross-section taken along the lines III—III of FIG. 1 showing the relationship between the various parts of the invention.

FIG. 4 is a cross-sectional view taken along the lines IV—IV of FIG. 1 showing the cylinder and elastomeric covering.

DETAILED DESCRIPTION OF THE INVENTION

Figure 1:
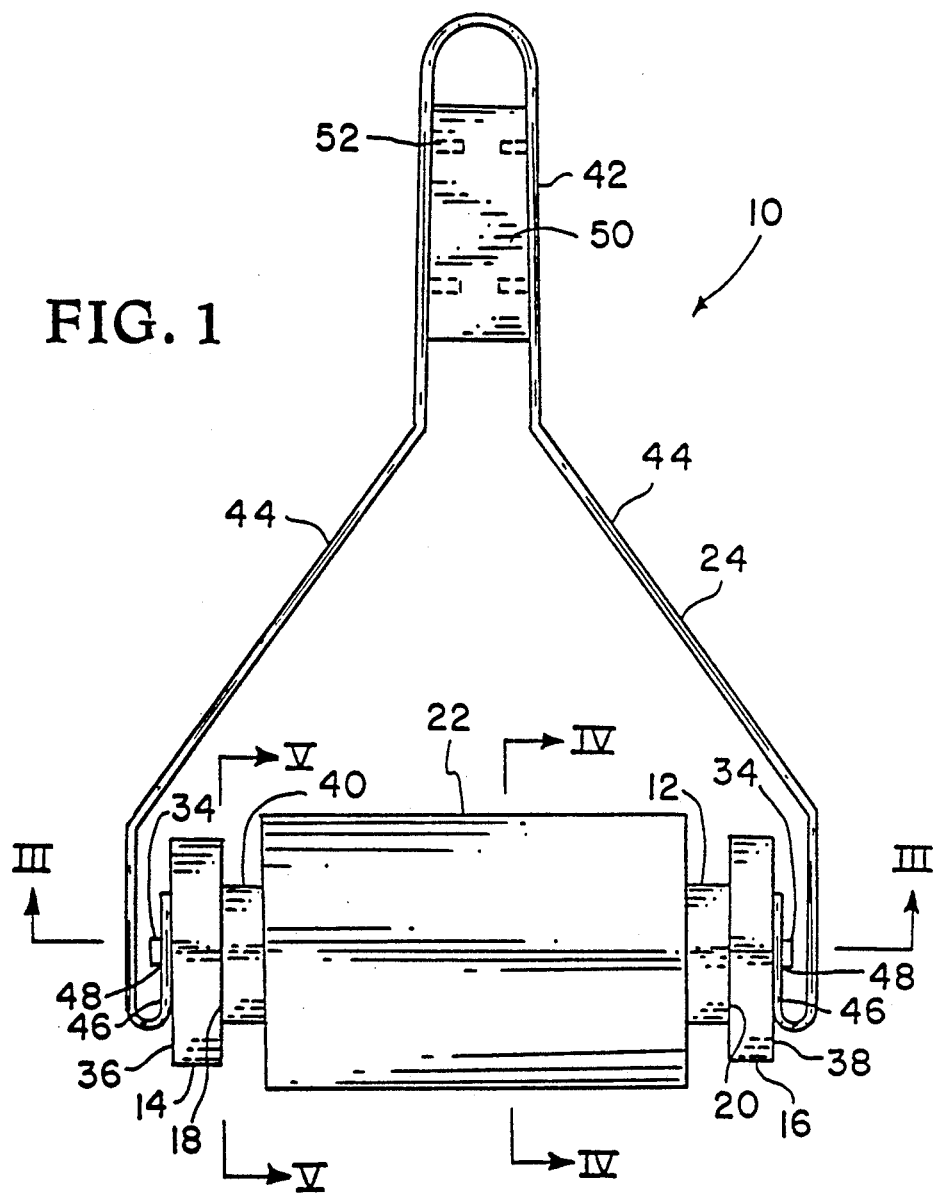
FIG. 1 is a top view of the preferred embodiment of the invention.

FIGS. 1, 2, and 3 illustrate one embodiment of a device for applying constant pressure to a surface generally designated by the numeral 10. Device 10 includes a cylinder 12. A first wheel 14 and a second wheel 16 are connected to each end 18 and 20 of cylinder 12. First and second wheels 14 and 16 have a diameter substantially greater than the diameter of cylinder 12. An elastomeric covering 22 surrounds cylinder 12. Elastomeric covering 22 has an outer diameter substantially greater than the diameter of first wheel 14 and second wheel 16. A handle 24 is coupled to wheels 14 and 16 for applying pressure to elastomeric covering 22.

More particularly, device 10 includes a cylinder 12 which has a longitudinal axis substantially greater than the diameter of cylinder 12 and is solid as illustrated in FIGS. 3 and 4. Cylinder 12 is preferably made from plastic or metal, however, any solid material will perform adequately. Cylinder 12 includes openings 13 and 15, as illustrated in FIG. 3, drilled into the center of each end 18 and 20.

Figure 5:
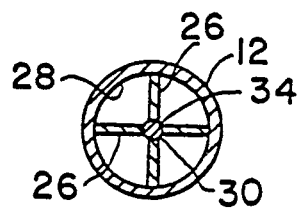
FIG. 5 is an end view in cross-section taken along the lines V—V of FIG. 1 showing an alternate embodiment of the cylinder.

Although it is preferred that cylinder 12 be solid it may also be hollow as illustrated in FIG. 5. In this embodiment cylinder 12 has an inner and outer diameter. Again it is preferred that cylinder 12 be made from plastic or metal. At the ends of cylinder 12 a pair of cross pieces 26 are connected in any conventional manner to the inner surface 28 of cylinder 12. A ring 30 is connected in any conventional manner to the inner ends of cross pieces 26. Ring 30 is used as a means for coupling wheels 14 and 16 to cylinder 12 as will be explained later.

First and second wheels 14 and 16 each has a diameter substantially greater than the diameter of cylinder 12 and each contains an opening 32 drilled through the center of wheels 14 and 16 as illustrated in FIG. 3. As illustrated in FIGS. 1, 2, and 3, a pin 34 having a diameter substantially the same as openings 13 and 15 in cylinder 12 and openings 32 in wheels 14 and 16 is inserted into openings 13 and 15 and cemented to cylinder 12 using any conventional adhesive. As illustrated in FIG. 5, Pin 34 is inserted into ring 30 and connected thereto in any conventional manner, such as, an adhesive or screws (not shown).

As illustrated in FIGS. 1 and 3, pin 34 has a length such that when wheels 14 and 16 are inserted on pin 34 through openings 32, pin 34 extends beyond the outer surface 36 and 38 of wheels 14 and 16, respectively. Wheels 14 and 16 are not permanently connected to pins 34 so that wheels 14 and 16 can be easily removed and replaced on pins 34. However, wheels 14 and 16 should fit snugly onto pins 34 so that when wheels 14 and 16 rotate cylinder 12 will also rotate.

As illustrated in FIGS. 1, 2, 3 and 4 an elastomeric covering 22 surrounds cylinder 12 and has an outer diameter substantially greater than the diameter of wheels 14 and 16. Elastomeric covering 22 may be attached to surface 40 of cylinder 12 in any conventional manner, such as, by an adhesive, or it may fit snug with friction to cylinder 40 without adhesive. Elastomeric covering 22 is compressible so that when pressure is applied to device 10 elastomeric covering 22 will compress. Preferably, elastomeric covering 22 is foam rubber. It is preferred that the foam rubber be sealed on the outer surface so that contamination can be easily removed from the foam rubber. However, if desired, the foam rubber may be unsealed.

As illustrated in FIGS. 1 and 2 handle 24 is used to apply pressure to elastomeric covering 22. Handle 24 includes a grip portion 42, arms 44 and tangs 46 located at the ends of arms 44. Tangs 46 include an opening 48 which fit over the ends of pins 34 so that pins 34 will rotate within tangs 46. Handle 24 may include a spacer 50 in grip portion 42 to make handle 24 more rigid. Spacer 50 may be attached to grip portion 42 in any conventional manner, such as, by screws 52.

In operation, an adhesive tape is placed with the sticky side on the surface where there is particulate contamination that is to be analyzed. The device 10 is placed over the tape so that the elastomeric covering 22 is in contact with the non sticky side of the tape. A person grips handle 24 on grip portion 42 and applies pressure compressing elastomeric covering 22 until wheels 14 and 16 contact the surface. Cylinder 12, elastomeric covering 22, and wheels 14 and 16 are rolled over the tape. The elastomeric covering 22 applies predetermined constant pressure to the tape and because it is elastomeric it conforms to any imperfections in the surface. Device 10 is then removed and the particulate contamination adhering to the tape can be accurately analyzed under a microscope.

The pressure applied by elastomeric covering 22 can be varied in several ways. The type and stiffness of the elastomeric covering 22 can be varied. In addition, the diameter of wheels 14 and 16 may be varied. If the diameter of wheels 14 and 16 are increased the pressure exerted by elastomeric covering 22 will be decreased and if the diameter of wheels 14 and 16 are decreased the pressure exerted by elastomeric covering 22 will be increased. Thus, several wheels 14 and 16 of varying diameter may be kept on hand to vary the pressure exerted by elastomeric covering 22.

A device for applying predetermined constant pressure to a surface has been described. Obvious modifications and variations of the device are possible in light of the above teachings. It is to be understood, therefore, that within the scope of the appended claims the device may be practiced otherwise than as specifically described and illustrated.

Accordingly, the invention having been described in its best embodiment and mode of operation, that which is desired to be claimed by Letters Patent is:

1. A device for applying constant pressure to a surface, comprising:
   a cylinder;
   a first and second wheel means coupled to each end of said cylinder, said first and second wheel means having a diameter substantially greater than the diameter of said cylinder;
   a compressible elastomeric covering surrounding said cylinder, said compressible elastomeric covering having an outer diameter substantially greater than said diameter of said first and second wheel means; and
   means for compressing said compressible elastomeric covering until said first and second wheel means contact said surface, said compressible elastomeric covering applying constant pressure to said surface independent of additional pressure exerted by a user after said first and second wheel means contact said surface.

2. The device of claim 1 wherein said cylinder is a solid rigid cylinder.

3. The device of claim 1 wherein said cylinder is a hollow rigid cylinder.

4. The device of claim 1 wherein said first and second wheel means are coupled to said ends of said cylinder by pin means.

5. The device of claim 4 wherein said means for applying pressure to said elastomeric covering is a handle means rotatably coupled to said pin means.

6. The device of claim 1 wherein said elastomeric covering is foam rubber.

7. The device of claim 6 wherein the outer surface of said foam rubber is sealed.

8. The device of claim 1 wherein said means for applying pressure to said elastomeric covering is a handle means rotatably coupled to said first and second wheel means.

9. The device of claim 1 wherein said elastomeric covering is coupled to said cylinder with an adhesive.

10. The device of claim 1 wherein said elastomeric covering is coupled to said cylinder by friction.

* * * * *